United States Patent [19]
Neckers et al.

[11] Patent Number: 5,955,002
[45] Date of Patent: Sep. 21, 1999

[54] METHOD FOR DETERMINING PROPERTIES OF A POLYMER COATING OR FILM CURED BY CATIONIC POLYMERIZATION

[75] Inventors: Douglas C. Neckers, Perrysburg; Kathleen G. Specht, Bowling Green; Kesheng Feng, Bowling Green; Roman Popielarz, Bowling Green, all of Ohio

[73] Assignee: Spectra Group Limited, Inc., Maumee, Ohio

[21] Appl. No.: 08/967,927

[22] Filed: Nov. 12, 1997

[51] Int. Cl.⁶ .................................................. G01N 21/64
[52] U.S. Cl. ...................................... 252/301.35; 436/172
[58] Field of Search ....................... 436/172; 252/301.16, 252/301.35

[56] References Cited

U.S. PATENT DOCUMENTS

| | | | |
|---|---|---|---|
| 4,250,382 | 2/1981 | Libby ........................................ | 250/302 |
| 4,651,011 | 3/1987 | Ors et al. .............................. | 250/459.1 |
| 4,922,113 | 5/1990 | Melancon ................................ | 250/372 |
| 5,037,763 | 8/1991 | Petisce ..................................... | 250/302 |
| 5,158,720 | 10/1992 | Levy ...................................... | 250/458.1 |
| 5,556,663 | 9/1996 | Chang et al. ............................... | 427/8 |
| 5,598,005 | 1/1997 | Wang et al. .............................. | 250/459 |
| 5,606,171 | 2/1997 | Neckers et al. ....................... | 250/459.1 |
| 5,633,313 | 5/1997 | Blanchard et al. ...................... | 524/719 |
| 5,707,587 | 1/1998 | Blanchard et al. ................... | 422/82.08 |

FOREIGN PATENT DOCUMENTS

| | | | |
|---|---|---|---|
| 54-145163 | 11/1979 | Japan .................................. | 250/458.1 |
| 1311932 | 3/1973 | United Kingdom ................ | 250/461.1 |

OTHER PUBLICATIONS

Zhang et al., *J. Imaging Sc. and Tech.*, 36, No. 4 (1992).
Paczkowski et al., *J. Polymer Sc. Part A: Polymer Chem.*, 31, 841–846 (1993).
Paczokwski et al., *Chemtracts–Macromolecular Chem.*, 3 75–94 (1992).
Loutfy, *Macromolecules*, 14, 270–275 (1981).
Song et al., Intramolecular Charge Transfer Complexes As Fluorescence Probes For UV and Visible Light Induced Acrylate Polymerization, (1994).*
Cantor et al., *Radtech Report*, 3, 28–29, (1997).

Primary Examiner—C. Melissa Koslow
Attorney, Agent, or Firm—Thompson Hine & Flory LLP

[57] ABSTRACT

A method for monitoring a property of a cationically curable composition comprising the steps of: adding a fluorescence probe to a cationically curable composition; measuring the intensity of the fluorescence emission of the probe at a wavelength at which intensity changes in response to changes occurring in the composition, wherein the fluorescence probe is a compound of the formula (I):

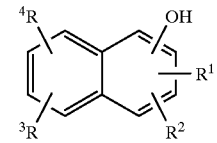

where $R^1$, $R^2$ and $R^3$ are the same or different and represent hydrogen, $C_1$–$C_{20}$ alkyl, $C_1$–$C_{20}$ alkoxyl, $C_2$–$C_{20}$ alkenyl, $C_2$–$C_{20}$ alkenoxyl, $C_3$–$C_{27}$ cycloaliphatic, $C_7$–$C_{27}$ aralkyl, $C_7$–$C_{27}$ aralkoxyl, $C_7$–$C_{27}$ alkaryl, or a substituted or unsubstituted diphenyl ether having the structure $R^9$—$C_6H_4$—O—$C_6H_4R^{10}$ where $R^9$ and $R^{10}$ may be hydrogen, alkyl, aryl or aralkyl; and $R^1$, $R^2$ and $R^3$ may be unsubstituted or may be substituted with or contain therein one or more atoms selected from the group consisting of O, S, N, OH, SH, $NH_2$, P, Cl, Br and I; and $R^4$ may be the same as $R^1$, $R^2$ and $R^3$; or $R^4$ may represent $COOR^5$, $CONR^5R^6$, $SO_2OR^5$, $SOOR^5$, $SONR^5R^6$, $SO_2NR^5R^6$ or $NR^5R^6$, where $R^5$ and $R^6$ may be hydrogen, alkyl, aryl or aralkyl; curing the composition; causing the probe to fluoresce; measuring the fluorescence of the probe; relating the change in intensity to a monitored property of the composition; and determining the monitored property of the composition, based upon the change in intensity.

11 Claims, 16 Drawing Sheets

1

METHOD FOR DETERMINING PROPERTIES OF A POLYMER COATING OR FILM CURED BY CATIONIC POLYMERIZATION

BACKGROUND OF THE INVENTION

The present invention relates to a method for monitoring degree of cure, and other properties of a coating or film cured by cationic polymerization using fluorescence methodologies.

Fluorescence spectroscopy has received considerable interest as an analytical tool due to its high sensitivity, selectivity and non-destructive characteristics. In addition, remote sensing is readily available using fluorescence methods through the use of fiber-optic cables to transmit optical signals to and from the analytical site in real time. Fluorescence spectroscopy has proven to be an extremely useful analytical tool in polymer chemistry. The technique has provided valuable information on the mechanisms and kinetics of polymerization, curing and crosslinking as well as oxidation, degradation and stabilization. The technique of fluorescence spectroscopy has been particularly useful in elucidating polymer properties such as their macro or supermolecular structure, molecular weight, viscosity and permeability.

Fluorescence probes as hereafter defined, have been used to study polymerization kinetics. For example, Paczkowski and Neckers, "Following Polymerization Kinetics of Multifunctional Acrylates in Real Time by Fluorescence Probe Methodology, *Macromolecules,* 25, 548–553 (1992) discusses the use of fluorescing probes such as dansylamide to follow the kinetics of polymerization and post-irradiation processes of multifunctional acrylates in real time. Other articles describe the use of fluorescence probes in polymerization studies of acrylates such as Paczkowski and Neckers, "Developing Fluorescence Probe Technology for Monitoring the Photochemical Polymerization of Polyolacrylates," *Chemtracts-Molecular Chemistry,* vol. 3, 75–94 (1992); Paczkowski and Neckers, "New Fluorescence Probes for Monitoring the Kinetics of Laser-Initiated Polymerization," *JPS: Part A: Polymer Chemistry,* vol. 31, 841–846 (1993); and Zhang, Kotchetov, Paczkowski and Neckers, "Real Time Monitoring of Polymerization Rates of Polyacrylates by Fluorescence Probes II. Effect of Depth of Polymerization for a Bleaching Photoinitiator System," *The Society for Imaging Science and Technology,* vol. 36, No. 4, 322–327, July/August 1992.

Various fluorescent probes have been developed recently for monitoring the progress of polymerization or final degree of cure of photocurable coating formulations cured by free radical polymerization. See, for example, U.S. Pat. No. 5,606,171. Typical fluorescent probes used for the free radically cured coating formulations contain basic amino functionality in their structure which is necessary to afford high fluorescence efficiency and large shift of the fluorescence spectrum with change in microviscosity and micropolarity of the probe environment. These probes are not useful for typical cationic cures because they interfere with the polymerization reaction. Thus, there is a need for a fluorescence probe which is useful in a process for determining degree of cure of a polymeric coating or film cured by cationic polymerization.

DEFINITION

The term "fluorescence probe" as used herein means a compound, the fluorescence characteristics of which, when added to a fluid solution, change in response to changes in the state of the solution. In accordance with the present invention, the changes in the fluorescent characteristics are related to changes in chemical, physical, and/or mechanical characteristics of the coating or film cured by cationic polymerization.

The term "cure" as used herein includes any cationic process by which a polymeric mass is hardened including, by way of example, crosslinking, or polymerization.

SUMMARY OF THE INVENTION

In accordance with the present invention, methods are provided for measuring the properties of an uncured, curing or a cured cationically polymerizable composition, such as a coating or film, using fluorescence methodologies, wherein a fluorescence probe is provided in the composition and the changes in the fluorescent characteristics of the probe are observed. Using previously prepared calibration curves, these changes can be related to various properties of the coating and particularly to the degree of cure. While the invention is principally applicable to monitoring the properties of coatings and films, those skilled in the art will appreciate that these properties can be measured in a polymeric mass of any geometry or shape provided, of course, that the mass, in at least one dimension, transmits the fluorescence in a manner or to such an extent that it can be detected. Hence, the invention broadly relates to the use of the disclosed methodologies in monitoring the properties such as degree of cure of a polymeric mass of any shape.

Using the foregoing fluorescence based methodologies, methods are provided whereby the properties of a coating can be monitored in an industrial setting. The method may be used in-line or off-line to enable the coating manufacturer to determine any variance in the coating and to adjust the coating parameters as necessary to correct for the variance. Among the coating parameters that might be adjusted in response to a detected variance are coating application rate, line speed, cure time, drying time, irradiation intensity, dosage, etc.

In one manifestation of the invention, fluorescence analysis is used to determine any of a number of properties of a film or coating cured by cationic polymerization such as the degree of cure, hardness, abrasion resistance, resistance to stain, tacticity, elasticity, molecular orientation, tensile strength, viscosity, modulus, stress state, wetness, resistance to smear or smudge, and others by relating the change in the fluorescence of a probe in the coating or film to a change in one or more of these properties. These properties may be measured individually, in combination, or in conjunction with the measurement of the coating thickness as previously described.

The ultimate properties of the polymeric network which constitutes a mass, such as a coating or film, depend on various factors, such as monomer structure, forms of initiation, reaction conditions and the rate and degree of cationic polymerization. These properties affect the microenvironment of the fluorescence probe and, thus, cause changes in its fluorescence. Probe fluorescence changes accompanying polymerization in photochemical processes, and others, are induced both by the solid polymers and the resulting polymeric solutions. By measuring the intensity of the fluorescence at two or more wavelengths and calculating the ratio of the intensities ($I_{\lambda a}/I_{\lambda b}$) for different predetermined coating or film-forming conditions such as degree of cure, hardness, tacticity, elasticity, etc., calibration curves can be constructed from which dynamic properties can be determined using fluorescence measurements. For example, by using such techniques as infrared transmission in thin films (FTIR), differential scanning calorimetry and the like, the degree of cure, for example, as indicated by double bond conversion can be determined. By correlating the measured property with fluorescence intensity ratios at two wavelengths or by recording the entire spectrum, for a given probe in a given coating composition, calibration curves can be established such that in an industrial setting, measurement of the intensity ratios can be used to monitor the degree of cure of the coating or film for in-line or off-line process control. In an analogous manner, calibration curves can be established relating fluorescence intensity ratios to other coating properties. Based upon such calibration data, the foregoing method can be used to monitor the properties of interest by an optical observation.

One manifestation of the invention is a method for monitoring a property of a cationically curable composition comprising the steps of:

adding a fluorescence probe to a cationically curable composition;

measuring the intensity of the fluorescence emission of the probe at a wavelength at which the intensity changes in response to changes occurring in the composition, wherein the fluorescence probe is a compound of the formula (I):

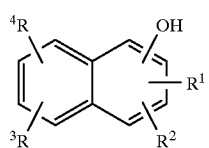

(I)

where $R^1$, $R^2$ and $R^3$ are the same or different and represent hydrogen, $C_1$–$C_{20}$ alkyl, $C_1$–$C_{20}$ alkoxyl, $C_2$–$C_{20}$ alkenyl, $C_2$–$C_{20}$ alkenoxyl, $C_3$–$C_{27}$ cycloaliphatic, $C_1$–$C_{27}$ aralkyl, $C_7$–$C_{27}$ aralkoxyl, $C_7$–$C_{27}$ alkaryl, or a substituted or unsubstituted is diphenyl ether having the structure $R^1$—$C_6H_4$—O—$C_6H_4R^{10}$ where $R^9$ and $R^{10}$ may be hydrogen, alkyl, aryl or aralkyl; and $R^1$,$R^2$ and $R^3$ may be unsubstituted or may be substituted with or contain therein one or more atoms selected from the group consisting of O, S, N, OH, SH, $NH_2$, P, Cl, Br and I; and $R^4$ may be the same as $R^1$, $R^2$ and $R^3$; or $R^4$ may represent $COOR^5$, $CONR^5R^6$, $SO_2OR^5$, $SOOR^5$, $SONR^5R^6$, $SO_2NR^5R^6$ or $NR^5R^6$ where $R^5$ and $R^6$ may be hydrogen, alkyl, aryl or aralkyl;

curing the composition;

causing the probe to fluoresce;

measuring the fluorescence of the probe;

calculating the ratio of the intensities of the fluorescence emission of the probe at two or more wavelengths;

relating the change in intensity to a monitored property of the composition; and determining the monitored property of the composition based upon the change in intensity.

In a particular embodiment of the invention, the intensity is measured at two wavelengths and the ratio of the intensities is calculated and related to the property being monitored.

The determination is made by comparing the observed intensity or the observed ratios to calibration data in which the intensity change or the ratios are correlated with an external measure of the property. This method can be used in combination with the method for determining the coating thickness if the fluorescence emission of the substrate in the first method is distinct from the fluorescence emission of the probe.

BRIEF DESCRIPTION OF THE DRAWINGS

FIG. 17C shows the fluorescence emission spectra of 0.5 wt % DDHNA both before cure and curing for 6 minutes as described in FIG. 15.

FIG. 17D shows the fluorescence emission spectra of 1.0 wt % DDHNA both before cure and after curing for 6 minutes as described in FIG. 15.

DETAILED DESCRIPTION OF THE INVENTION

Figure 1:
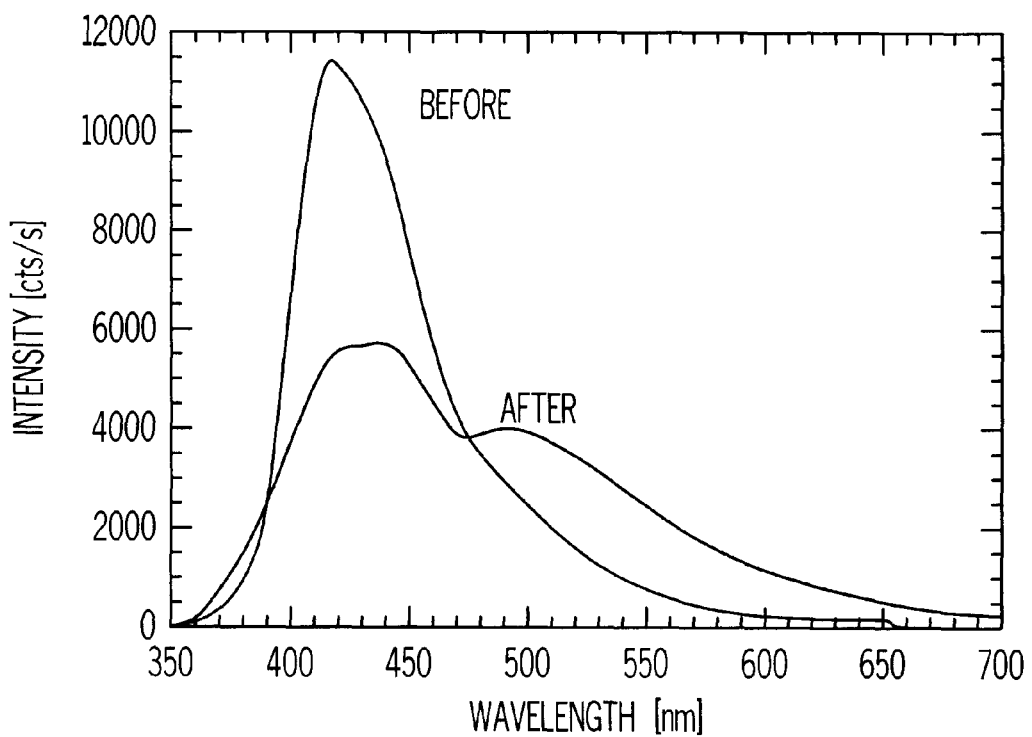
FIG. 1 shows fluorescence spectra of DDHNA in an epoxy silicone resin before and after cure using CM 1000 cure monitor.

It has been discovered that the degree of cure and other properties of polymeric masses, such as coatings and films cured by cationic polymerization, can be accurately and quickly measured using fluorescence methodology and the cationic fluorescence probes of this invention.

Often solid polymers are made in continuous processes from liquids which can be formed, shaped, delivered, or in some other way manipulated in the liquid, and then dried or cured to form the solid functional product. This process of conversion from a mobile phase to an immobile phase is herein defined as curing. Cured polymeric coatings are used in a variety of applications to provide a durable surface without detracting from the object itself. For example, coatings or films photohardenable by cationic polymerization such as epoxysilicones are used as adhesives; protective, decorative and insulating coatings; glass lamination; magnetic recording compositions; potting compounds; sealants; photoresists; wire insulation; can linings; textile coatings; laminates; impregnated tapes; printing plates; imaging materials and other applications for photohardenable compositions such as release coatings.

In order to coat a substrate, it is necessary, not only to have a method for coating the particular substrate in the mobile uncured phase and curing it to an immobile phase (be that solid, liquid, or gel) but, in many cases, it is also necessary to be able to accurately and quickly determine the degree of cure of the coating and other properties as a measure of the curing efficiency and effectiveness.

Monomers which can be polymerized by a cationic mechanism can be classified according to their functionality. They include cyclic ethers, cyclic formals and acetals, vinyl ethers, and epoxy compounds. These monomers can be made monofunctional, difunctional and multifunctional. They may also be large molecular weight prepolymers and oligomers. Examples of cationically polymerizable compounds include epoxy compounds, vinyl or allyl monomers, vinyl or allylic prepolymers, vinyl ethers, vinyl ether functional prepolymers, cyclic ethers, cyclic esters, cyclic sulfides, melamine-formaldehyde and phenol-formaldehyde resins, cyclic organosiloxanes, lactams and lactones, cyclic epoxysilicones and acetals and epoxy functional silicone oligomers, and mixtures thereof.

Epoxy monomers are the most important class of polymerizable substrates. These materials are readily available as commodity items, and the resulting cured polymers possess excellent dimensional and thermal stability as well as superior mechanical strength and chemical resistance. They are widely used in the coating, painting and adhesives industry. The relationship between structure and reactivity in epoxy monomers is a complex function of several factors. The reactivity of an epoxy monomer is not only determined by the electronic nature of its particular epoxy group, its steric accessibility and the initiating species used, but also by properties like the basicity, the nucleophilicity of other functional groups which coexist in the monomer. In general, epoxidized diolefins are most reactive, followed by epoxidized diolefins containing acetal and ester linkage followed finally by diglycidyl ethers.

Examples of cationically polymerizable epoxy compounds described in the literature include any monomeric, dimeric or oligomeric or polymeric epoxy material containing one or a plurality of epoxy functional groups. Examples of polymerizable epoxy compounds include bisphenol-A-diglycidyl ether, trimethylene oxide, 1,3-dioxolane, 3,4-epoxycyclohexylmethyl-3',4'-epoxycyclohexyl carboxylate, phenyl glydicyl ether, 4-vinyl cyclohexene dioxide, limonene dioxide, cycloaliphatic epoxides such as 1,2-cyclohexene oxide, epichlorohydrin, glycidyl acrylate, glycidyl methacrylate, styrene oxide, allyl glycidyl ether, etc. Resins which result from the reaction of bisphenol A (4,4'-isopropylidenediphenol) and epichlorohydrin, or from the reaction of low molecular weight phenol-formaldehyde resins (Novolak resins) with epichlorohydrin have been used alone or in combination with an epoxy containing compound.

Examples of epoxysilicones and epoxy functional silicone oligomers having epoxy equivalent weights (EEW) of about 800 to 1,500 include dimethyl,-methyl-2-(7-oxabicyclo{4.1.0}heptan-3-yl) ethyl and have been found to be operable in the present invention. Dimethyl, methyl-2-(7-oxabicyclo{4.1.0}heptan-3-yl) ethyl having epoxy equivalent weights within the designated range may be purchased commercially from General Electric. In particular, dimethyl, methyl-2-(7-oxabicyclo{4.1.0}heptan-3-yl) ethyl having epoxy equivalent weights (EEW) of 900, 1100 and 1300 are available from General Electric under the tradenames UV9300, UV9315 and UV9400, respectively.

Useful hydride curable silicones include those mentioned in U.S. Pat. No. 4,504,645. Specific ethylenically-unsaturated silicon compounds may contain as few as one silicon atom, such as vinylpentamethyldisiloxane, 1,3-divinyl-tetramethyldisiloxane, 1,1,3-trivinyltrimethyldisiloxane, 1,1,3,3-tetravinyldimethyldisiloxane or polysiloxane precursors, as well as high molecular weight polysiloxanes containing up to 10,000 or more silicon atoms per molecule and having a molecular weight in the range of 150 to 10,000,000, preferable 200 to 2,000,000. Among cyclic materials, tetramethyltetraallylcyclotetrasiloxane, and tetramethyltetravinylcyclotetrasiloxane are included. Preferred compounds are vinyldimethyl end blocked polydimethylsiloxane fluids of 50 to 10,000 cP, most preferably 200 to 5,000 cP. Also preferred are vinyldimethyl end blocked polydimethylsiloxane fluids with up to 50 percent, preferable up to 20 percent, by weight of the dimethylsiloxy units replaced by diphenylsiloxy or methylphenylsiloxy units. Also included within the scope of ethylenically-unsaturated polysiloxanes are cyclic compounds containing silicon-bonded vinyl or allyl radicals, such as the cyclic trimer, tetramer, or pentamer of methylvinylsiloxane $[(CH_2=CH)(CH_3)SiO]_w$ or methylallysiloxane $[(CH_2=CH-CH_2)(CH_3)SiO)_w]$ wherein subscript w is an integer of 3 to 10.

Polyhydrosiloxanes useful in the present invention include 1,3-dimethyldisiloxane, 1,1,2,2-tetramethyldisiloxane, as well as high polymers containing up to 10,000 or more silicon atoms per molecule including hydrogen siloxane units $(HSiO_{1.5})$, methylhydrogen siloxane units $(HSiCH_3O)$ dimethylhydrogen siloxane units $[HSi(CH_3)_2O_{-0.5}]$, methylhydrogen siloxane units $(H_2SiO)$, such as $(CH_3)_3SiO[Si)CH_3)(HO]_{3.5}Si(CH_3)_3$. Also included are cyclic materials such as cyclic polymers of methyl hydrogen siloxane having the formula $(CH_3SiHO)$, wherein subscript w is an integer from 3 to 10.

Such epoxysilicones and epoxy functional silicone oligomers are commercially available from General Electric and are described in ACS PMSE Proceeding 1989, Vol. 60, pp. 217,222.

In addition, polymerizable epoxy compounds include polymeric materials containing terminal or pendant epoxy groups. Examples of these compounds are vinyl copolymers containing glycidyl acrylate or methacrylate as one of the comonomers. Other classes of epoxy containing polymers amenable to cure have also been described in the literature and include epoxy-siloxane resins, epoxy-polyurethanes and epoxy-polyesters. Such polymers usually have epoxy functional groups at the ends of their chains. Epoxy-siloxane resins and the method for making them are more particularly shown by E. P. Plueddemann and G. Ganger, J.Am. Chem. Soc. 81 632–5 (1959), and in Crivello et al., Proceeding ACS, PMSE, 60, 217 (1989).

As described in the literature, epoxy resins can also be modified in a number of standard ways such as reactions with amines, carboxylic acids, thiols, phenols, alcohols, etc. As shown in U.S. Pat. Nos. 2,935,488; 3,235,620; 3,369,055; 3,379,653; 3,398,211; 3,403,199; 3,563,850; 3,567,797; 3,677,995, etc. Further examples of epoxy resins are shown in the Encyclopedia of Polymer Science and Technology, Vol. 6, 1967, Interscience Publishers, New York, pp. 209–271.

Examples of vinyl or allyl organic monomers which have been used in the literature in the practice of the cationic polymerization include, for example, styrene; vinyl acetamide; methylstyrene; isobutyl vinyl ether; n-octyl vinylether; acrolein; 1,1-diphenylethylene; R-pinene, vinyl arenes such as 4-vinylbiphenyl, 1-vinylpyrene, 2-vinylfluorine, acenapthylene, 1- and 2-vinyl-napthalene; 9-vinyl carbazole; vinyl pyrrolidone; 3-methyl-1-butene; vinyl cycloaliphatics such as vinylcyclohexane, vinylcyclopropane, 1-phenylvinylcyclopropane; dienes such as isobutylene, isoprene, butadiene, 1,4-pentadiene, 2-chloroethyl vinyl ether, etc.

Some of the vinyl organic prepolymers which have been described are, for example, $CH_2=CH-O-(CH_2O)_n-CH=CH_2$, where n is a positive integer having a value up to about 1000 or higher; multifunctional vinylethers, such as 1,2,3-propane triol trivinyl ether, trimethylolpropane trivinyl ether, polyethylene glycol divinyl ether (PEGDVE), triethylene glycol divinyl ether (TEGDVE), vinyl ether-polyurethane, vinyl ether-epoxy, vinyl ether-polyester, vinyl ether-polyether and other vinyl ether prepolymers such as 1,4-cyclohexane dimethanol-divinylether commercially available from GAF and others, and low molecular weight polybutadiene having a viscosity of from 200 to 10,000 centipoises at 25° C., etc.

A further category of cationically polymerizable materials are cyclic ethers which are convertible to thermoplastics. Included by such cyclic ethers are, for example, oxetanes such as 3,3-bis-chloromethyloxetane alkoxyoxetanes as shown by U.S. Pat. No. 3,673,216; oxolanes such as tetrahydrofuran, oxepanes, oxygen containing spiro compounds, trioxane, dioxolane, etc.

In addition to cyclic ethers, there are also included cyclic esters such as lactones, for example, propiolactone, cyclic amines, such as 1,3,3,-trimethylazetidine and cyclic organosiloxanes, for example. Examples of cyclic organosiloxanes include hexamethyl trisiloxanes, octamethyl tetrasiloxane, etc. Cyclic acetals may also be used as the cationic polymerizable material.

Examples of other materials which are cationically cured include glycidyl methacrylates, epoxy acrylates, acrylated melamine formaldehyde and epoxidized siloxanes.

Industrial applications in which fluorescence methodologies of the present invention are useful in monitoring degree of cure include: coating floor tiles and flooring with an abrasion-resistant (no-wax) finish coating papers and films with epoxysiloxane release coatings or finishes to provide release sheets useful in the tape and label industries.

In measuring the degree of cure of a cationically photo-hardenable polymeric mass such as a coating or film material, a fluorescence probe is incorporated into the cationically curable polymeric composition. The fluorescence probe is generally added to the coating material in the amount of 0.1 to 0.5% by weight of the coating material. This methodology can also be used to monitor the properties of multiple coatings on one substrate.

In accordance with the present invention, the relatively narrow fluorescence spectrum of the probe before curing generally becomes much broader after curing. Thus, cure monitoring with the present fluorescence probes is based on a change in intensity or the spectral shape change or spectral shift. In certain instances simple intensity changes at one wavelength without a spectral shift can be used to follow cure. In other cases a spectral shift occurs upon curing and a ratio at two wavelengths will relate to the monitored property. The probes useful in determining the degree of cure of a cationically polymerizable compound appear to work by a different mechanism than those probes used in free radical polymerization. It is believed that unlike the probes used for free radical polymerization, which apparently respond by a change in physical properties resulting in a blue shift in the emission spectrum of the probe as the resin polymerizes, the probes used in cationic polymerizations appear to undergo a chemical reaction concomitant with cure with the formation of a second emission band with a maximum further to the red of the original emission maximum. In the present invention, the probe displays a marked concentration dependence which is not observed in the free radical probes. Furthermore, the cationic fluorescence probes useful in the invention have good solubility in both polar and highly non-polar media making such probes suitable for curable compositions of various polarity.

Cure monitoring results obtained in accordance with the invention are highly reproducible and appear to correlate well with the degree of cure. At low probe concentrations (about 0.1 wt % to 0.5%) the probe is very sensitive with a large span in ratio between the uncured and cured states.

The fluorescence probes useful in the invention do not contain amino groups or other groups which would react with a proton and display fluorescence characteristics which change in parallel with changes in the polymer matrix. The probes found to be particularly useful are illustrated by the formula (I):

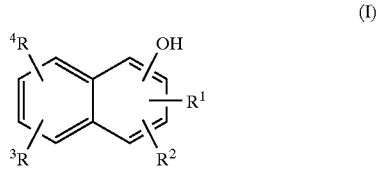

where $R^1$, $R^2$ and $R^3$ are the same or different and represent hydrogen, $C_1$–$C_{20}$ alkyl, $C_1$–$C_{20}$ alkoxyl, $C_2$–$C_{20}$ alkenyl, $C_2$–$C_{20}$ alkenoxyl, $C_3$–$C_{27}$ cycloaliphatic, $C_7$–$C_{27}$ aralkyl, $C_7$–$C_{27}$ aralkoxyl, $C_1$–$C_{27}$ alkaryl, or a substituted or unsubstituted diphenyl ether having the structure $R^9$—$C_6H_4$—O—$C_6H_4R^{10}$ where $R^9$ and $R^{10}$ may be hydrogen, alkyl, aryl or aralkyl; and $R^1$, $R^2$ and $R^3$ may be unsubstituted or may be substituted with or contain therein one or more atoms selected from the group consisting of O, S, N. OH, SH, $NH_2$, P, Cl, Br and I; and $R^4$ may be the same as $R_1$, $R^2$ and $R^3$; or $R^4$ may represent $COOR^5$, $CONR^5R^6$, $SO_2OR^5$, $SOOR^1$, $SONR^5R^6$, $SO_2NR^5R^6$ or $NR^5R^6$, where $R^5$ and $R^6$ may be hydrogen, alkyl, aryl or aralkyl. Examples of cationic probes include all derivatives of dihydroxynaphthalene (1,2; 1,3; 1,4; 1,5; 1,6; 2,3; 2,6; 2,7) 1-naphthol-3,6-disulfonic acid; 2-hydroxy-1-naphthaldehyde; 5-hydroxy-1-naphthalenesulfonic acid; 6-hydroxy-2-naphthalenesulfonic acid; 1-hydroxy-2-naphthoic acid; 2-hydroxy-2-naphthoic acid; 3-hydroxy-2-naphthoic acid-1'-hydroxy-2'-acetonaphthone; 2'-hydroxy-1'acetonaphthone; 1,8-dihydroxynaphthalene-3,6-disulfonic acid; 3,6-dihydroxynaphthalene-3,6-disulfonic acid; 6,7-dihydroxy-2-naphthalenesulfonic acid; 1,4-dihydroxy-2-naphthoic acid; and 3,5-dihydroxy-2-naphthoic acid. A particularly preferred cationic probe is N-dodecyl-1-hydroxy-2-naphthalene-carboxamide (DDHNA). N-dodecyl-1-hydroxy-2-naphthalenecarboxamide (DDHNA) is sold by Aldrich as a technical grade beige solid containing about 90% of pure ingredient. The DDHNA is readily soluble in non-polar solvents due to its dodecyl side chain. The solubility in hexane at room temperature was estimated as 5.9 g DDHNA/100 mL hexane, which corresponds to about 8.0 wt % solution. The solubility increases upon heating, and, above 60° C. the DDHNA melts, which makes it miscible with non-polar solvents in almost any proportion. The large increase of DDHNA solubility with increase of temperature can be used for further purification of the probe by crystallization whenever higher grade product is necessary.

The fluorescence probe technology can be used for on-line analysis in both quality control and processing optimization. An on-line monitoring of the degree of cure or any of the other properties previously mentioned can be achieved by continuously or periodically examining the fluorescence emission spectra of the probe which was doped into the monomer resin at a low concentration (typically 0.1–0.5 wt. %) before the photocuring process.

The apparatus for measuring cure includes a source of excitation energy, an analytical head which will preferably access multiple sites on a coated substrate of any size and shape, a detector for measuring the emitted radiation, and data processing software so that the monitored polymer property may be determined at any point along the substrate by comparison to calibration data. The detected radiation wavelengths will vary with the nature of the substrate or support as well as with the selection of the probe. Any fluorescent wavelengths of measurable intensity are useful. The apparatus may be designed to detect selected wavelengths in the emission spectrum or to detect the entire spectrum. The apparatus may optionally include an alarm circuit which is set to generate a signal if the comparison with the calibration data indicates that there is an unacceptable variance in the monitored polymer property. Alternatively, the alarm circuit can interface with other controls to adjust any of the polymer processing conditions previously mentioned so as to directly effect a correction of the variance.

Any convenient source of energy which will activate the fluorescence emission of the probe may be employed and any means capable of detecting the fluorescence emission can be used in the present invention. Suitable examples of excitation sources include ultraviolet radiation, electron beam radiation, particle beam radiation, visible light, lasers (e.g., an argon laser), etc.

The apparatus may employ a bifurcated optical fiber array wherein one set of fibers provides the excitation energy to the substrate or coating and another associated set of fibers is coupled to a photodetector and detects fluorescence. This array may assume any design configuration necessary to accommodate the substrate being coated. However, the array will likely be housed in a light-tight chamber. In one embodiment a linear array of optical fiber pairs (i.e., one fiber for excitation and the other for detection) may be positioned immediately adjacent to the coated substrate for monitoring in the production environment.

The apparatus may include other components of a conventional fluorimeter such as an electronic shutter, a monochromator, a photomultiplier tube, a photodiode array or CCD as the radiation detector, analog to digital converters which interface with the detector, focusing lenses, interference filters, neutral density filters, etc. A commercially available cure monitor that is useful in the present invention is available from Spectra Group Ltd., Inc., Maumee, Ohio, under the tradename CM 1000.

While the following examples will reference the measurement of degree of cure, those skilled in the art will appreciate that any of the aforesaid properties can be calibrated and measured in an analogous manner. The degree of cure of a polymer can be determined by the fluorescence change exhibited in a cured polymer. The degree of cure can be obtained from a coordinate calibration curve as shown in the examples below.

EXAMPLE 1

A photocurable diepoxy silicone resin containing 0.11 wt % of DDHNA-probe and 2.3 wt % of GE Silicones UV9380C photocatalyst solution UV9380C containing 2-isopropylthioxanthanone and bis (4-docecylphenyl) iodonium hexafluorantimonate photoinitiator was prepared. A 0.1 mm layer of the formulation between glass slides was cured in a UV-box with two 450 W Hg-lamps for 15 min. Fluorescence spectra of the sample were recorded before and after cure using a CM 1000 Cure Monitor. The spectra are shown in FIG. 1.

It is noticeable from FIG. 1 that the fluorescence spectrum of the DDHNA probe is significantly altered upon cure.

Instead of the relatively narrow fluorescence spectrum seen before cure, after cure the spectrum is much broader and a second emission band appears. Thus, cure monitoring with the DDHNA probe is based on the change in the spectral shape.

Figure 2:
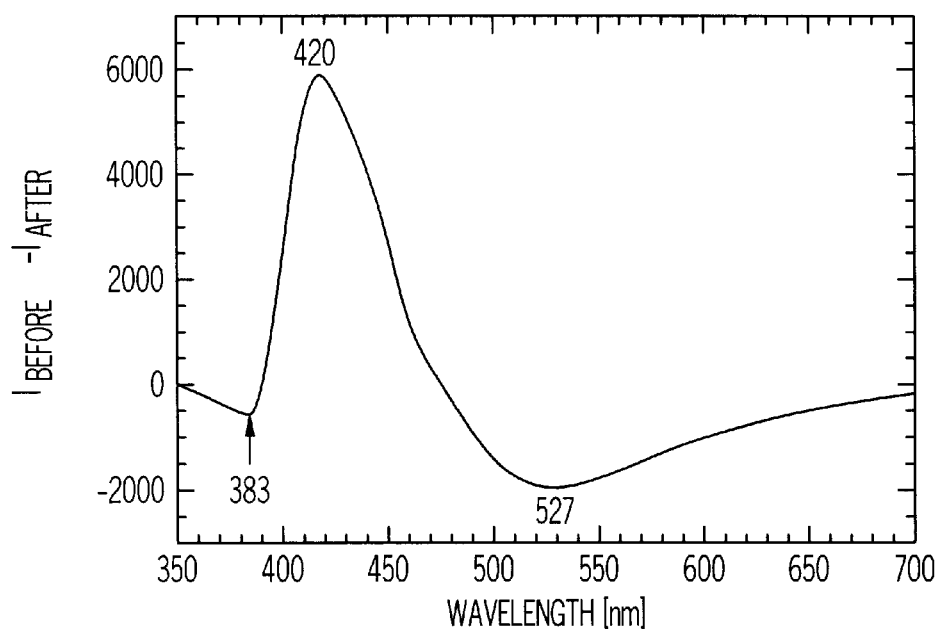
FIG. 2 illustrates the differential spectrum of DDHNA in an epoxy silicone resin in which the spectrum after cure is subtracted from the spectrum before cure for the purpose of finding the wavelengths at which maximal change in the fluorescence intensity occurs upon cure.

The intensity ratio method has been selected for cure monitoring with the DDHNA probe. In order to find the optimal monitoring wavelengths, the spectrum after cure was subtracted from the spectrum before cure and the difference spectrum is shown in FIG. 2. Either the fluorescence intensity ratio at 383/420 nm or the ratio at 527/420 nm can be used, but the second ratio has been selected, because this ratio affords higher monitoring sensitivity. It has to be pointed out, that in the case of DDHNA probe, fluorescence intensity at a longer wavelength is divided by the intensity at a shorter wavelength for the ratio, unlike in the case of typical probes used for resins cured by free radical methods.

Applicability of the DDHNA probe for monitoring of cationic polymerization was tested by curing 0.1 mm layer of the epoxysilicone formulation with an excitation beam of the CM 1000 set at 350 nm. A small spot within the sample tested was irradiated continuously with the excitation beam, while fluorescence intensity ratios were taken at the rate of 1 scan/sec. The change of the fluorescence intensity ratio ($I_{527}/I_{420}$) as a function of time is shown in FIG. 3.

Figure 3:
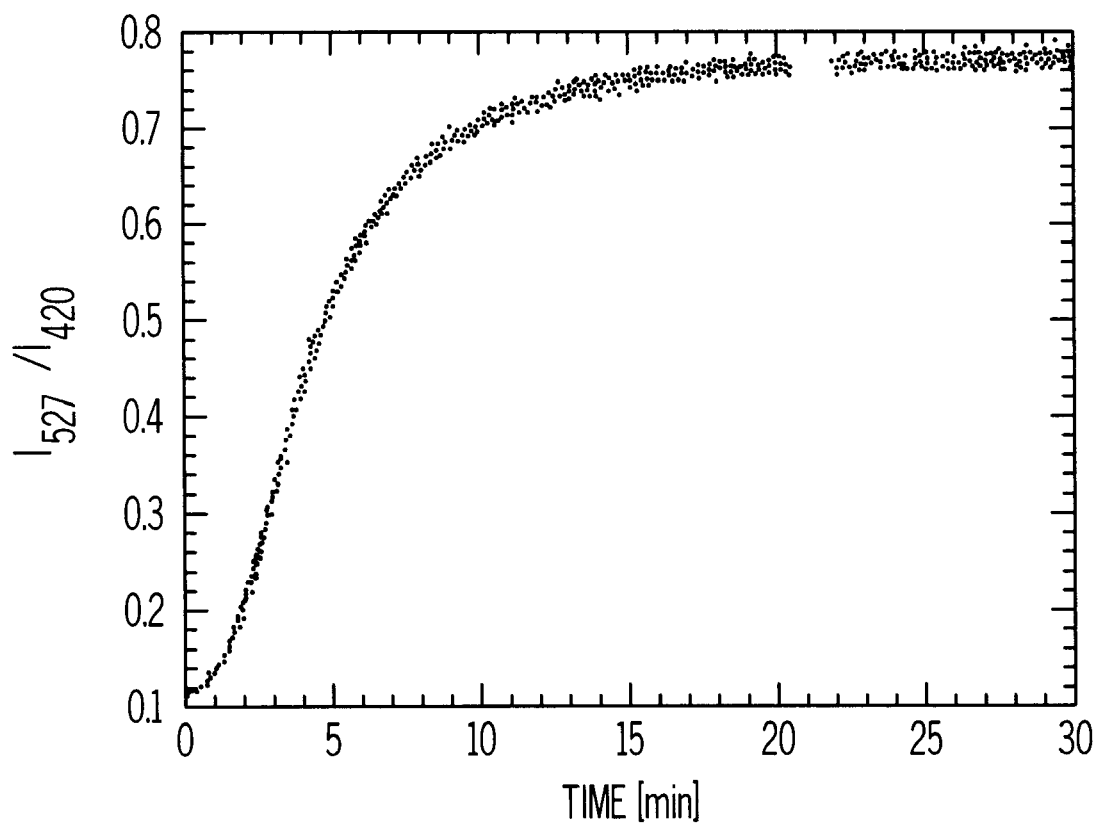
FIG. 3 illustrates the change of the fluorescence intensity ratio as a function of time.

FIG. 3 represents the first instance of real-time monitoring of curing progress of an epoxysilicone resin under steady-state irradiation conditions, by using the Cure Monitor alone. In the case of dansyl-probe derivatized epoxysilicone resins, studied previously, the polymerization was too slow to be completed within reasonable time under the same irradiation conditions.

The curing profile obtained using DDHNA (FIG. 3) has all the features one can expect from a cationic photopolymerization under steady-state irradiation conditions. The curing of the resin is catalyzed by a protic acid generated from the photoinitiator. Initially, when the irradiation is started, there is no free acid catalyst in the medium, As more and more acid is generated from the photoinitiator upon irradiation, the polymerization accelerates as indicated by increasing the slope of the curing profile. However, with polymerization progress the reactive functional groups are consumed and less and less of the groups remain in the medium causing a decrease in the curing kinetics. Finally, when all of the reactive groups are consumed, the curing profile reaches a plateau. The fluorescence intensity ratio for the DDHNA probe in the epoxysilicone resin changed from about 0.1 to 0.8, when going from the non-cured to a cured state of the resin. Such large change (i.e., 8-times) will afford enough monitoring sensitivity to resolve even small differences in degree of cure.

EXAMPLE 2

Figure 4:
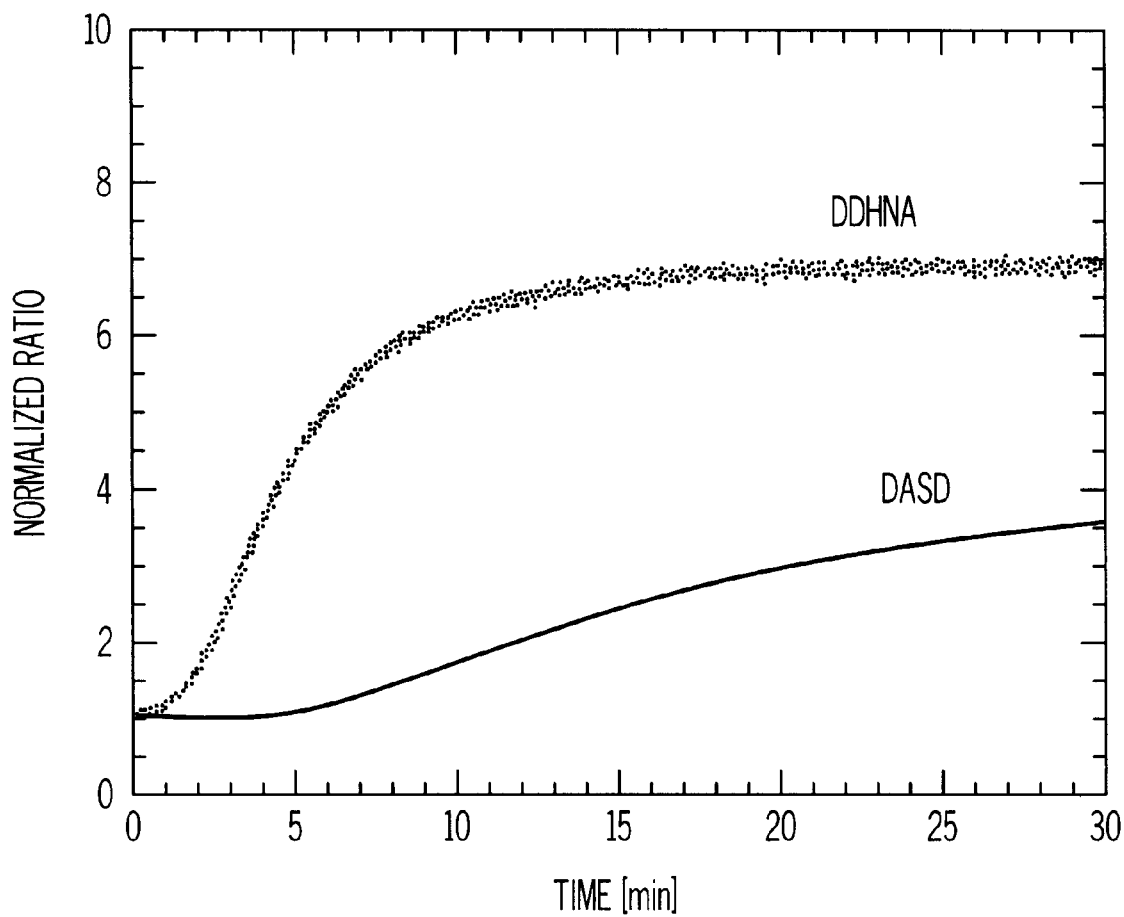
FIG. 4 illustrates comparison of curing kinetics of the same epoxysilicone formulation using different probes.

FIG. 4 compares the curing kinetics of the same epoxysilicone formulation using different probes. One formulation contained 0.11 wt % of DDHNA probe, while the other formulation contained 0.11 wt % of N,N-dimethylamino-n-butyl sulfamido naphthalene, DASD. All other components of the formulations as well as the curing conditions were identical. The excitation beam of the CM 1000 set at 350 nm was used to cure the resin. For relative comparisons, the ratios were normalized by dividing each ratio by the corresponding ratio before cure. A comparison of fluorescence intensities at the peak maximum for DDHNA and DASD probes indicated that before cure the intensity of DDHNA probe was about ⅔ of the corresponding intensity of DASD probe in the same resin and at the same probe concentration. After cure the intensity of the DDHNA probe corresponds to about ⅓ of the intensity of DASD probe in the same resin and at the same probe concentration, which means that the DDHNA probe has a slightly lower fluorescence efficiency than the DASD probe in epoxysilicone resins. However, the DASD probe is not suitable for cationic polymerization because of the interaction of the amine group of the DASD probe with the acid catalyst which slows down the cationic polymerization (FIG. 4). The slightly lower fluorescence efficiency of the DDHNA probe is however insignificant compared to its advantages. It can be noticed immediately from FIG. 4, that while in the case of DDHNA the resin was practically cured within the first 15 min. of irradiation, the resin doped with DASD did not reach a plateau even after 30 min. of irradiation. Moreover, in the case of using DASD the epoxysilicone did not start curing within the first 5 min.; there is a clear induction period before the polymerization starts. This indicates that the basic amino groups present in the DASD structure neutralized the acid catalyst generated within the first 5 min.; only after the probe had been protonated could the excess acid start catalyzing the cationic polymerization. The DDHNA probe does not inhibit cationic polymerization.

The relatively large difference in curing kinetics between the resin formulations containing DASD and DDHNA probes is hard to account for by only 0.1% content of each probe in the presence of large excess (i.e., 2.3%) of photoinitiator. This indicates that the difference is caused by both an inhibition of the curing kinetics in the presence of DASD and an acceleration of the curing kinetics in the presence of DDHNA.

EXAMPLE 3

Cationic photopolymerization catalyzed by an acid-generating photoinitiator usually does not stop immediately after the light exposure has ceased, but the acid formed keeps catalyzing the polymerization for some time. Thus, one can expect that the fluorescence intensity ratio measured with a fluorescent probe immediately after cure will still increase to some extent with time until the acid catalyst is deactivated in termination (or other) reactions, or until all reactive monomer functionalities are used up.

Applicability of the DDHNA-probe for monitoring the post-cure changes occurring in an epoxysilicone coating was tested in comparison to behavior of DASD-probe. A 0.1 mm layer of an epoxysilicone resin containing a photoinitiator and a probe was cured by direct exposure to two 450 W Hg-lamps for 15 min., and next, the changes occurring in the sample after exposure upon standing at room temperature in the dark were monitored with the CM 1000. The fluorescence intensity ratios were scanned every 5 min. for over 17 hours. Relative changes in the ratios normalized to the initial ratio value immediately after exposure are plotted as a function of time in FIG. 5.

Figure 5:
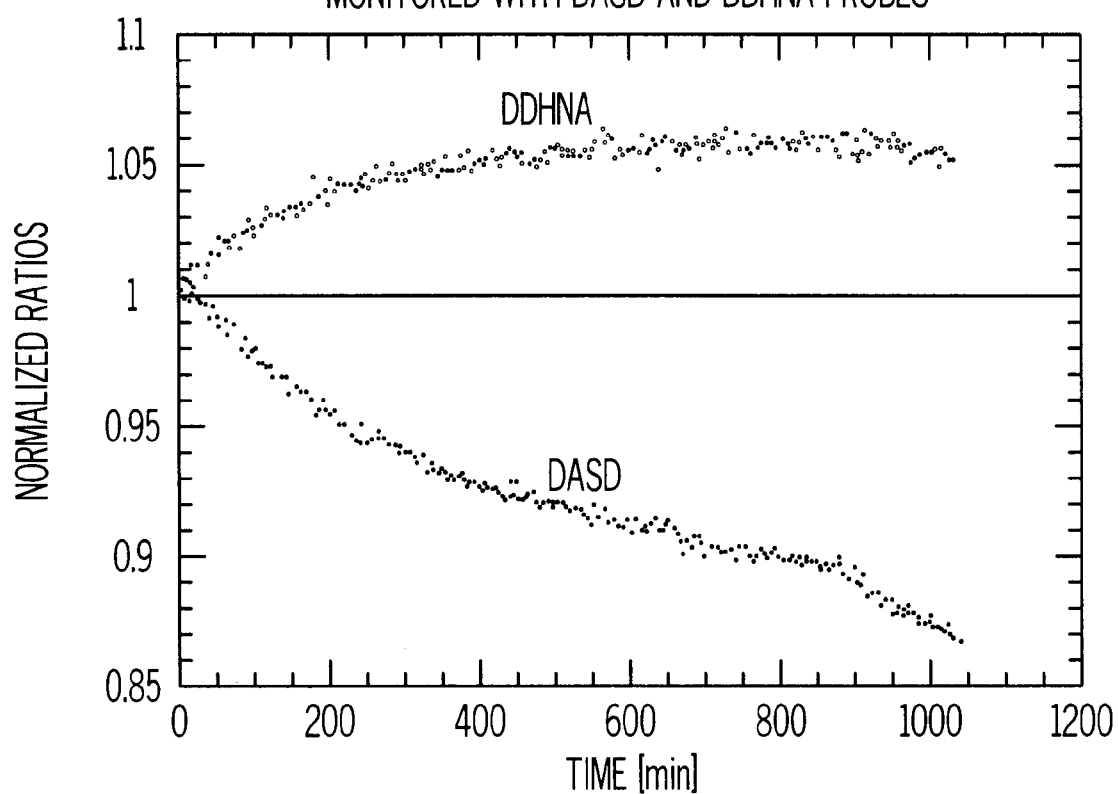
FIG. 5 illustrates the slow post-cure changes in the coating in terms of the ratios normalized to the initial ratio value immediately after exposure plotted as a function of time.

FIG. 5 indicates that DDHNA response is what one could expect for the post-cure effect. The fluorescence intensity ratio increased by about 6% and then stabilized at a constant value. On the other hand, the response of DASD is rather unusual; the ratio indicated by DASD decreased with time. This indicates that the response of DASD is affected by the acid catalyst present in the medium, and, that the DASD response in cationically cured resins depends to some extent not only on physical changes of microviscosity and micropolarity of the medium, but also of chemical changes like reversible probe protonation. DDHNA does not contain basic amino groups in its structure, which makes it insensitive to the acid.

EXAMPLE 4

GE Silicones Low Release Epoxysilicone resin, UV9300 containing 0.1 wt % N-dodecyl-1-hydroxy-2-naphthalenecarboxamide (DDHNA) probe and 2 wt % photocatalyst solution containing 2-isopropylthioxanthanone and bis (4-dodecylphenyl) iodonium hexafluroantimonate was heated to 70° C. to fully dissolve DDHNA and the photoinitiator in the silicone resin.

Samples 6A and 6B were prepared by placing a large drop of the resin formulation between two glass microscope slides with labels approximately 10 mils thick labels at the ends of the slides.

Figure 6A:
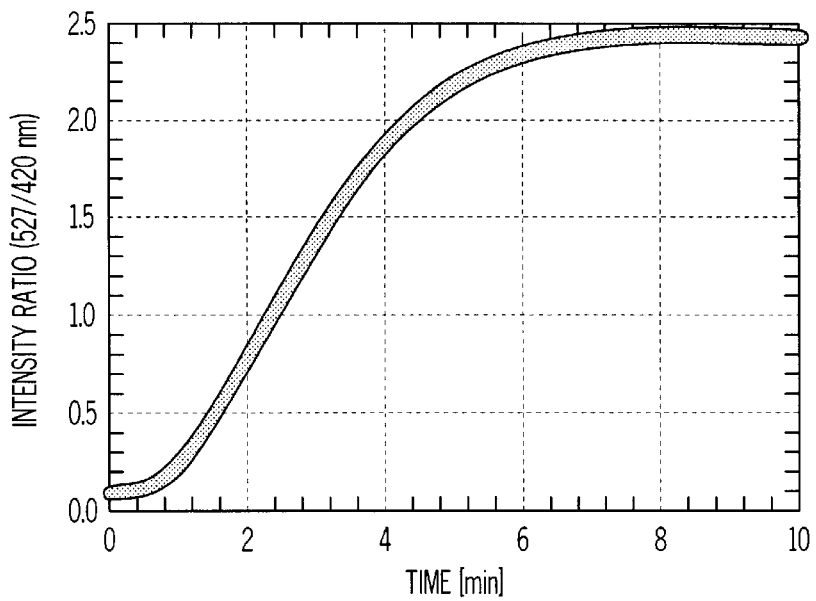
FIG. 6A illustrates the cure profile obtained using 0.1 wt % DDHNA probe in the GE Silicones epoxysilicone resin UV9300. The sample was cured using the 350 nm excitation light of the CM 1000 while simultaneously collecting the cure profile date.

FIG. 6A shows the cure profile of the sample cured using the 350 nm excitation band of a CM 1000 cure monitor while simultaneously monitoring the fluorescence emission intensity. A cure time of about 7.5 minutes was required to fully cure the sample as seen by the plateau on the graph. After approximately 8 minutes, the overcured sample turned orange at the irradiation point, probably due to isopropylthioxanthone (ITX) coloration. This coloration affects the ratio causing the slight downward trend observed in the graph at long irradiation times.

Figure 6B:
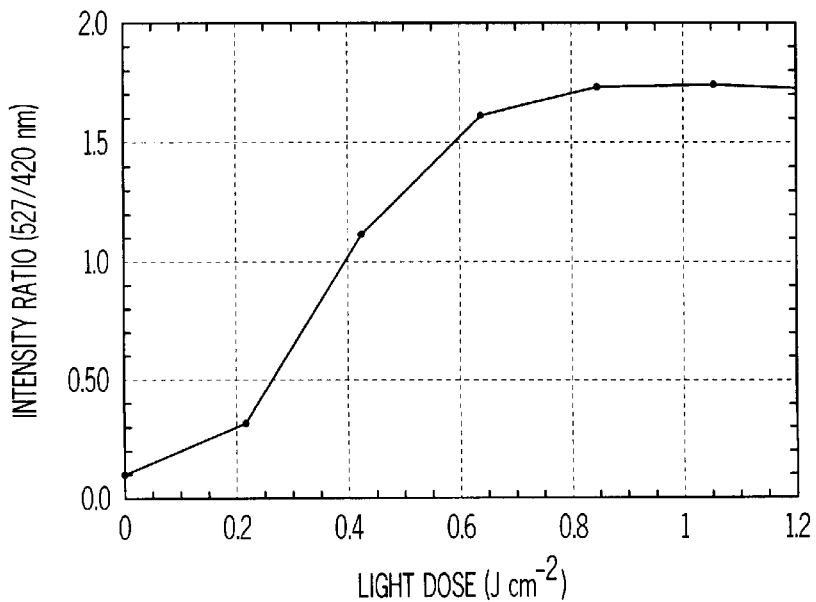
FIG. 6B illustrates the cure profile obtained using 0.1 wt % DDHNA probe in the GE Silicones epoxysilicone resin UV9300. The sample was cured with a Fusion D bulb at a speed of 160 feet per minute. The fluorescence ratio was measured on the CM 1000 after each pass under the curing light source.

FIG. 6B shows the results of curing a sample of the same resin by passing through a Fusion light system with a 300 watt D bulb at 160 feet per minute. Each pass was 212 mJ cm$^{-2}$ over the range of 200–600 nm as determined using a modified IL 390 Light Bug. The fluorescence intensity was monitored before cure and after each pass through the Fusion system to generate the kinetic cure profile plotted in FIG. 6B. The kinetic profile is similar to that shown in FIG. 6A. The large difference in ratio between the cured and uncured state is particularly noteworthy, indicating very good sensitivity of the DDHNA probe at this concentration.

EXAMPLE 5

Figure 7:
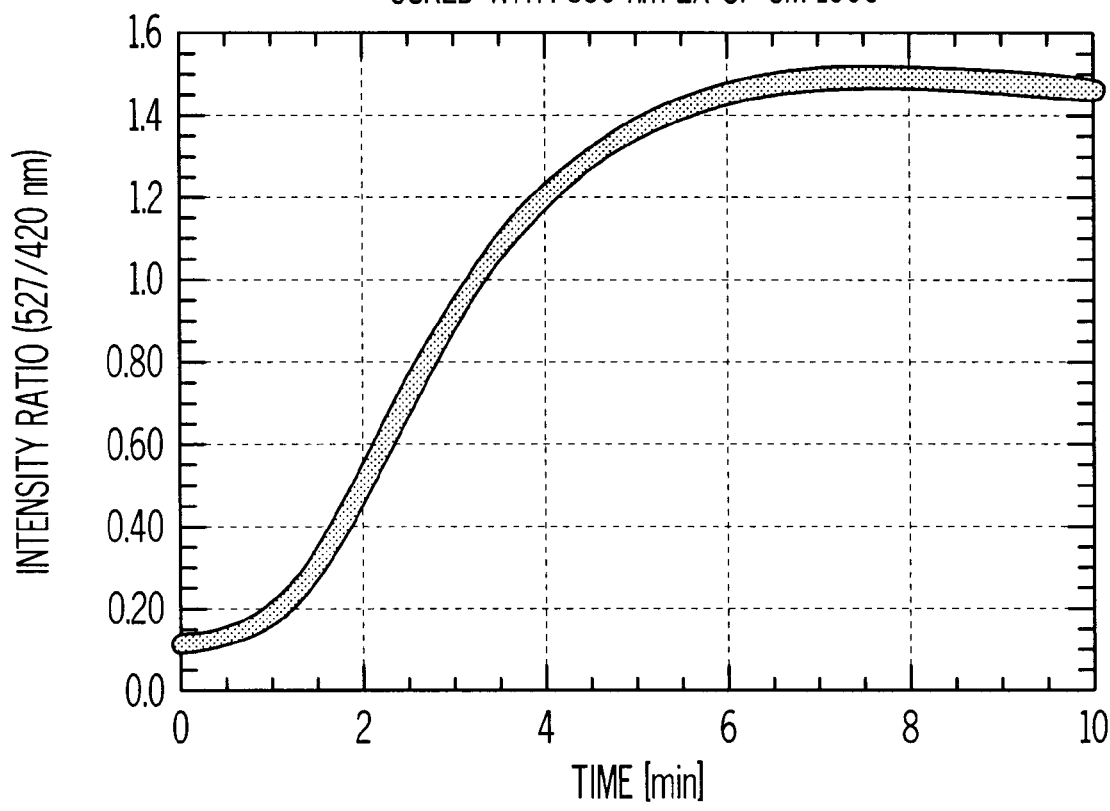
FIG. 7 illustrates the cure profile obtained using 0.1 wt % DDHNA probe in the GE Silicones epoxysilicone resin UV9315. The sample was cured using the 350 nm excitation light of the CM 1000 while simultaneously collecting the cure profile data.

The procedure of Example 4 was repeated except that GE Silicones medium Release Epoxysilicone resin UV9315, which is similar to UV9300 except the epoxy equivalent weight is 1100, was employed. The cure profile of this resin cured with 350 mm excitation band of the CM 1000 is shown in FIG. 7. The results are similar to those shown for the UV 9300 resin described in Example 4.

EXAMPLE 6

Figure 8:
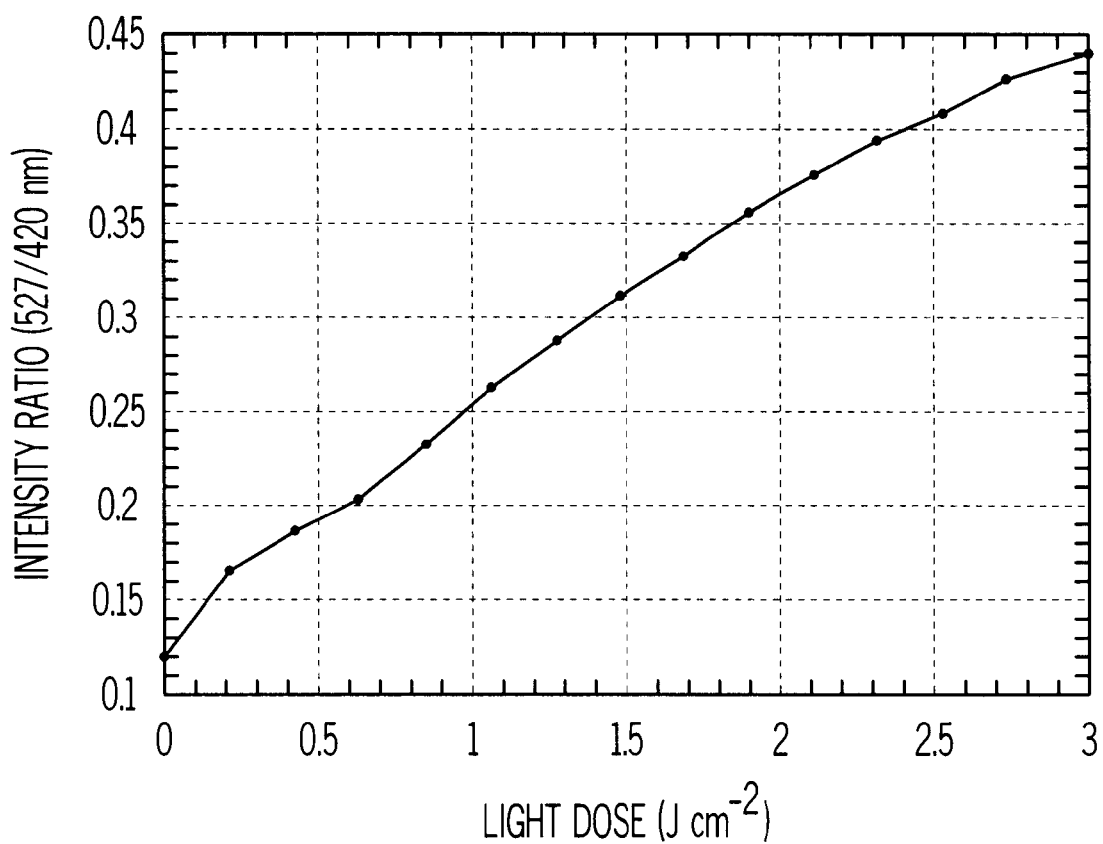
FIG. 8 illustrates the cure profile obtained using 0.1 wt % DDHNA probe in a silicone acrylate resin. The sample was cured with a Fusion D bulb at a speed of 160 feet per minute. The fluorescence ratio was measured on the CM 1000 after each pass under the curing light source.

The procedure of Example 4 was repeated using a Silicone Acrylate mixture containing hexanediacrylate and methyl polysiloxanes. In this case scotch tape was used as a spacer to give approximately 2.5 mil space samples between glass slides as described in the previous example. After 14 passes under the Fusion D bulb (3 mJ cm$^{-3}$) the resin was not fully cured. This can be seen in FIG. 8 as the fact that the ratio is still increasing and never reaches a plateau.

EXAMPLE 7

Figure 9:
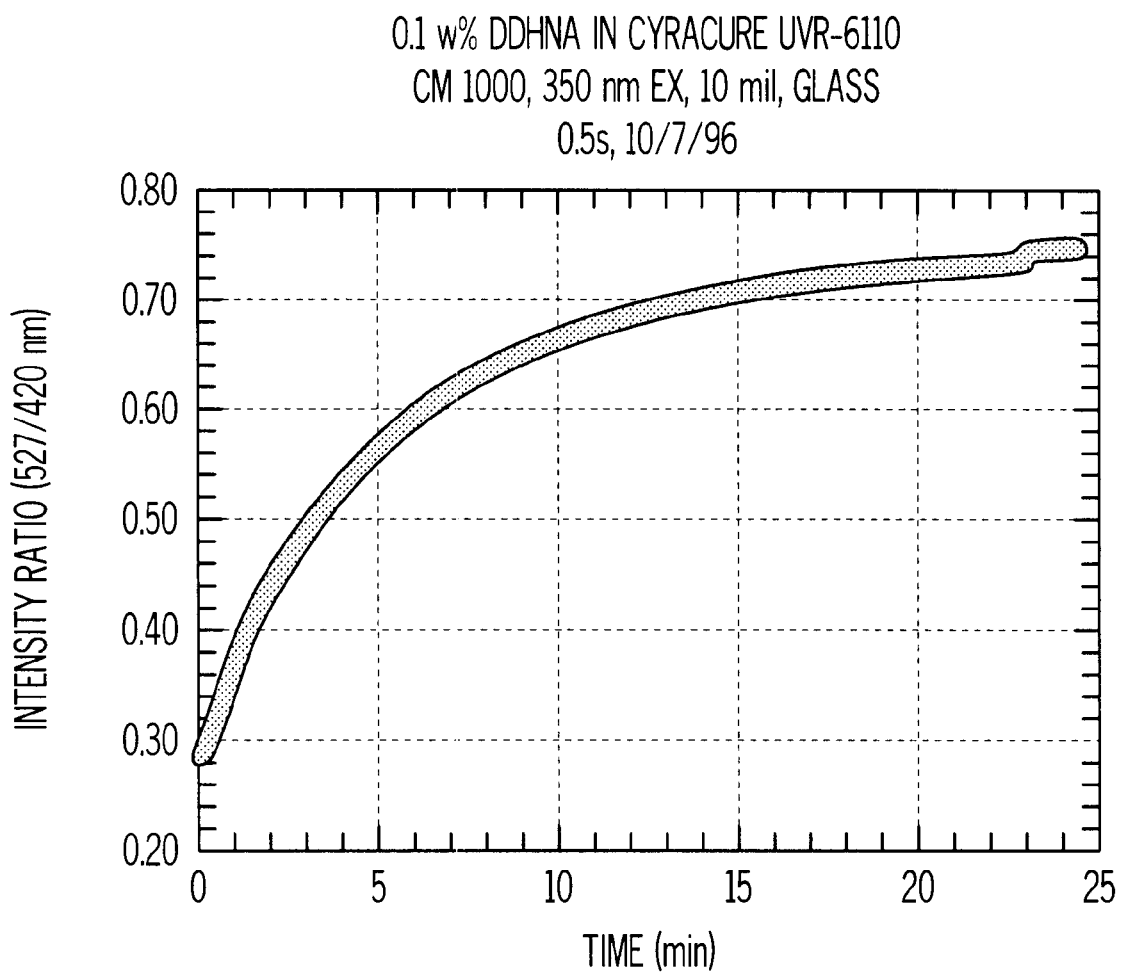
FIG. 9 illustrates the cure profile obtained using 0.1 wt % DDHNA probe in Union Carbide resin Cyracure UVR-6100. The sample was cured using the 350 nm excitation light of the CM 1000 while simultaneously collecting the cure profile data.

The procedure of Example 4 was repeated except that a cycloaliphatic epoxy resin from Union Carbide was cationically polymerized. The resin consisted of approximately 75 wt % Cyracure UV-6110 (3,4-Epoxy cyclohexyl methyl-3, 4-Epoxy cyclohexyl carboxylate and 25 wt % Tone Polyol (polycaprolactone triol). The cure profile obtained by curing the 350 mm excitation beam of the CM 1000 is shown in FIG. 9. In contrast to the sample shown in FIG. 6, no induction period is observed in the sample. From the graph it appears that more than 20 min. are required to fully cure the sample.

EXAMPLE 8

Figure 10:
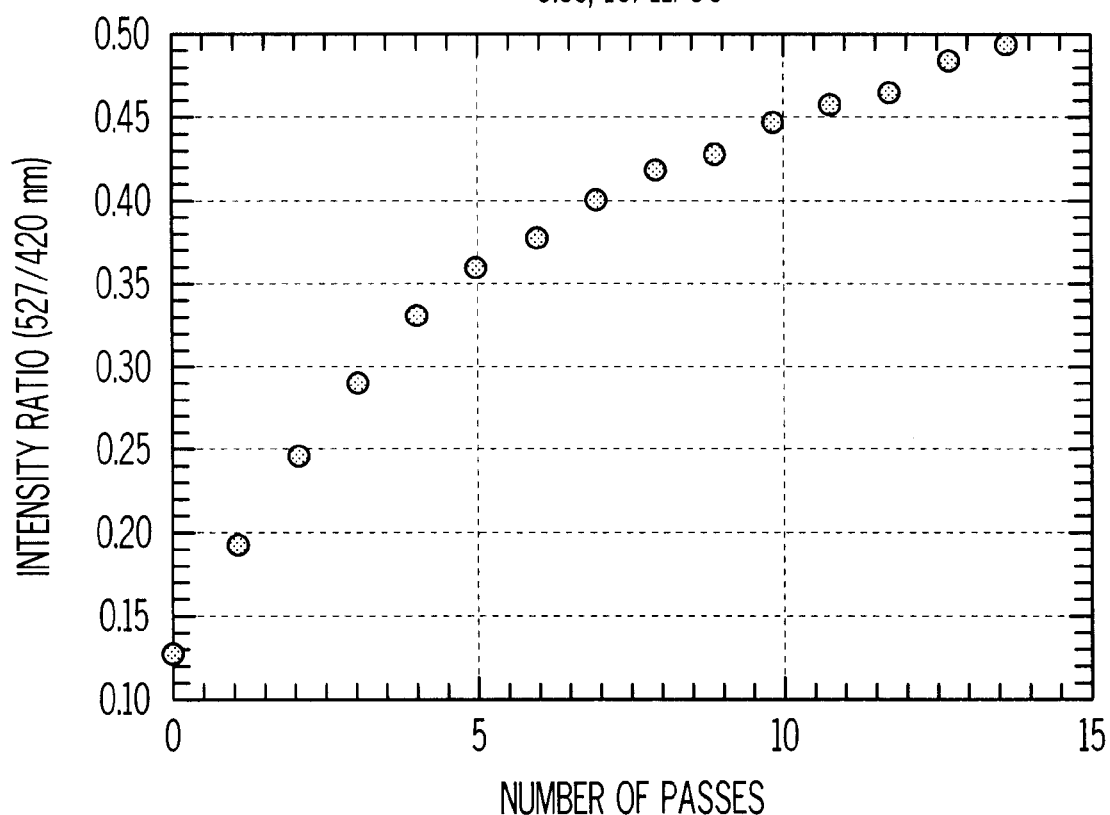
FIG. 10 illustrates the cure profile obtained using 0.1 wt % DDHNA probe in Dow epoxy novolac (D.E.N.) 438-EK85. The sample was cured with a Fusion D bulb at a speed of 80 per minute. The fluorescence ratio was measured on the CM 1000 after each pass under the curing light source.

The procedure of Example 4 was repeated except that the cationically polymerizable resin was D.E.N.® 438-EK85, an epoxy novolac resin available from Dow. The sample was cured by passing the sample through a fusion light system with a 300 watt D bulb at 80 feet per minute. The cure profile for the samples is shown in FIG. 10.

EXAMPLE 9

Figure 11:
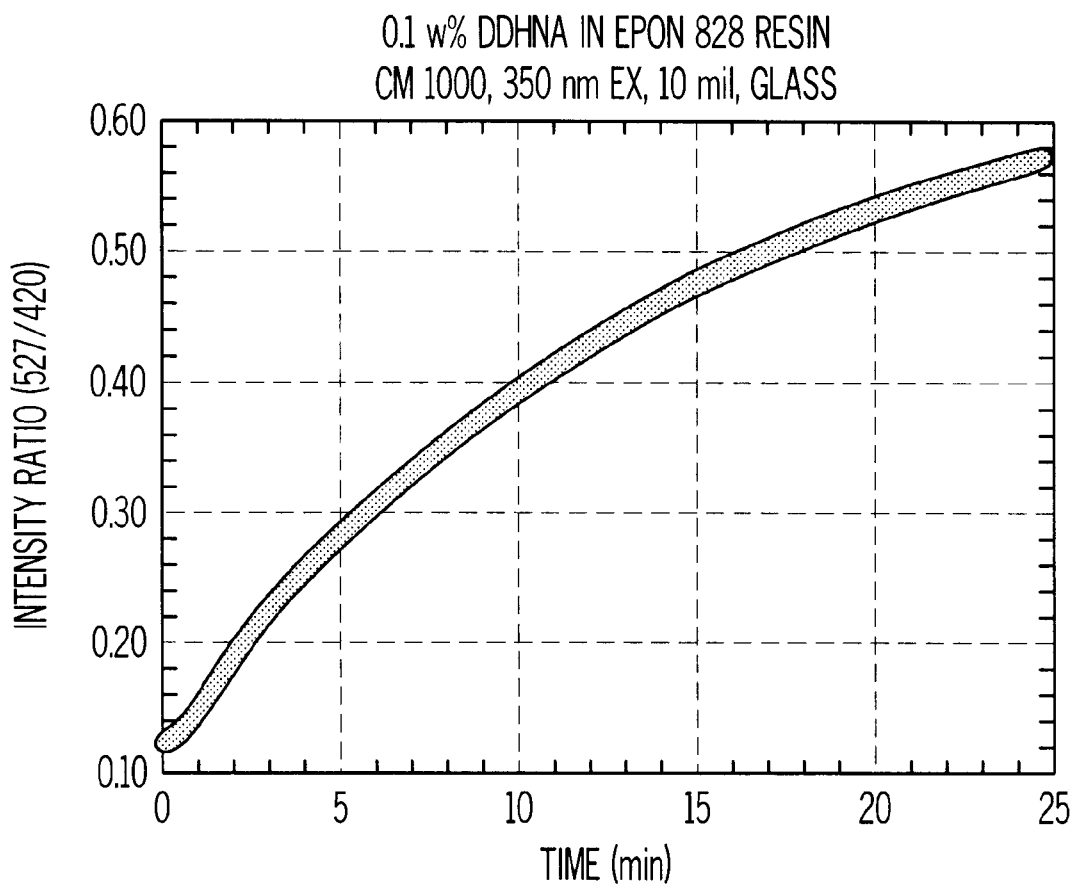
FIG. 11 illustrates the cure profile obtained using 0.1 wt % DDHNA probe in Shell Resin EPON™ 828 (bisphenol A diglycidyl ether) with GE Silicones photocatalyst solution UV9380C which contains thioxanthone and an iodonium salt. The sample was cured using the 350 nm excitation light of the CM 1000 while simultaneously collecting the cure profile data.

The procedure of Example 4 was repeated except that the cationically polymerizable resin was a bisphenol A diglycidyl ether available from shell under the Tradename EPON 828. The cure profile for a sample cured with the 350 mm excitation beam of the CM 1000 is shown in FIG. 11.

EXAMPLE 10

Figure 12:
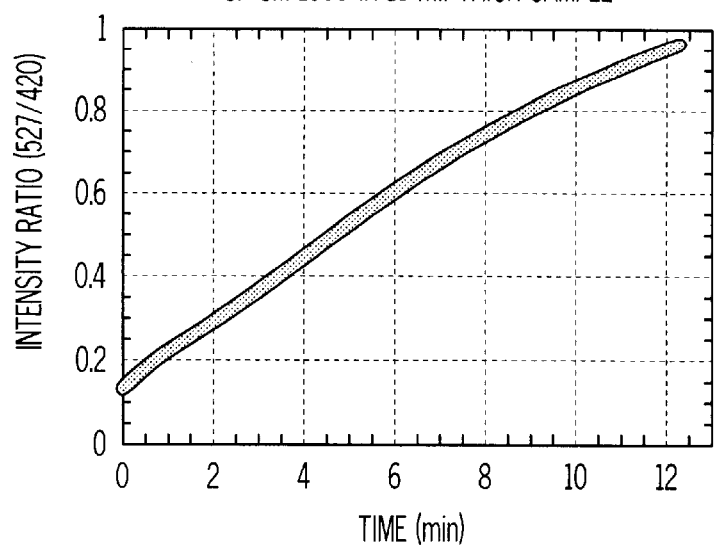
FIG. 12 illustrates the cure profile obtained using 0.1 wt % DDHNA probe in Shell Resin Epon™ Resin 160 (multifunctional novolac resin) with Union Carbide sulfonium salt UVI 6974. The sample was cured using the 350 nm excitation light of the CM 1000 while simultaneously collecting the cure profile data.

The procedure for Example 4 was repeated except that the cationically polymerizable resin was a multifunctional novolac resin from Shell under the trade name EPON 160 and instead of the iodonium salt a sulfonium salt was used as the photoinitiator. The sulfonium salt can be directly excited at the 350 nm excitation wavelength rather than having to be sensitized by the thioxanthone. These results are plotted in FIG. 12. The results are very similar to the previous example and indicate that the DDHNA probe is capable of monitoring cure with several different initiators.

EXAMPLE 11

Figure 13:
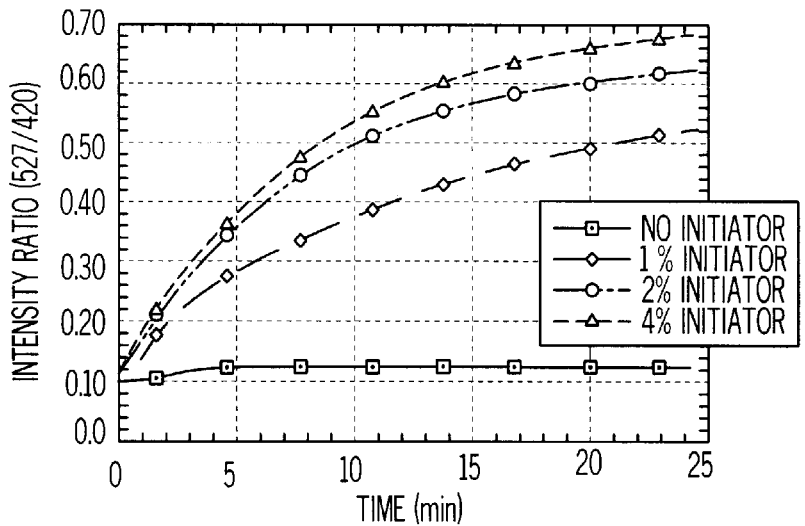
FIG. 13 shows the cure profiles of four different samples of Union Carbide cycloaliphatic epoxy resin Cyracure UVR- 6110 containing GE Silicones photocatalyst UV9380C at three different concentrations (1%, 2%, 4%) and the control without catalyst. All samples were 10 mils thick, contained 0.1 wt % DDHNA probe and were cured with the 350 nm excitation light from the CM 1000.

The procedure of Example 7 is followed except that the photoinitiator concentration is varied. In these experiments three samples were made which contained 1, 2 and 4 w % of the thioxanthone/iodonium salt initiator UV9380C. A control without initiator was also irradiated. All samples were exposed to the 350 nm excitation beam of the CM 1000 for 25 minutes while collecting the fluorescence emission data. As shown in FIG. 13, the rate of cure was dependent on the initiator concentration; increasing with higher concentration of photoinitiator. Minimal change in ratio was observed for the control sample. This follows the expected trend and again is an indication that the changes observed in the DDHNA probe can be used to monitor cure of cationically polymerized samples.

EXAMPLE 12

Figure 14:
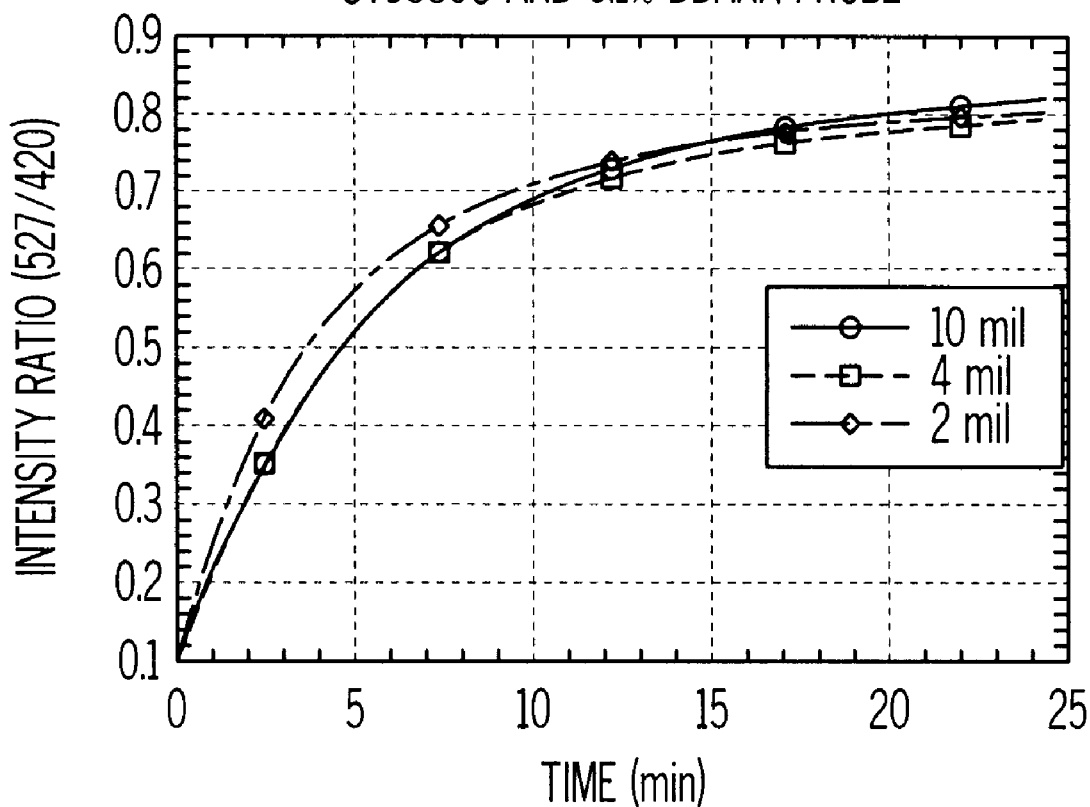
FIG. 14 shows the cure profile of the same resin as that used in FIG. 13 with 2 wt % initiator. In this case the sample thickness was varied between 2 and 10 mils as shown in the legend.

The procedure of Example 7 is followed except that the sample thickness is varied. Three samples of thickness 2 mil, 4 mil and 10 mil were made by using different spacers on the ends of the glass slides. All samples were exposed to 350 nm light from the CM 1000 for 25 minutes. The cure profiles are plotted in FIG. 14. As expected the rates of cure are roughly similar. This indicates that the sample thickness does not affect the DDHNA fluorescence emission, another indication that this is a useful probe for monitoring cure.

EXAMPLE 13

The procedure of Example 4 was repeated except the probe concentration was varied. In this case 4 mil thick samples containing 0.1, 0.25, 0.5 and 1.0 w % DDHNA were cured using the 350 nm excitation beam of the CM 1000.

Figure 15:
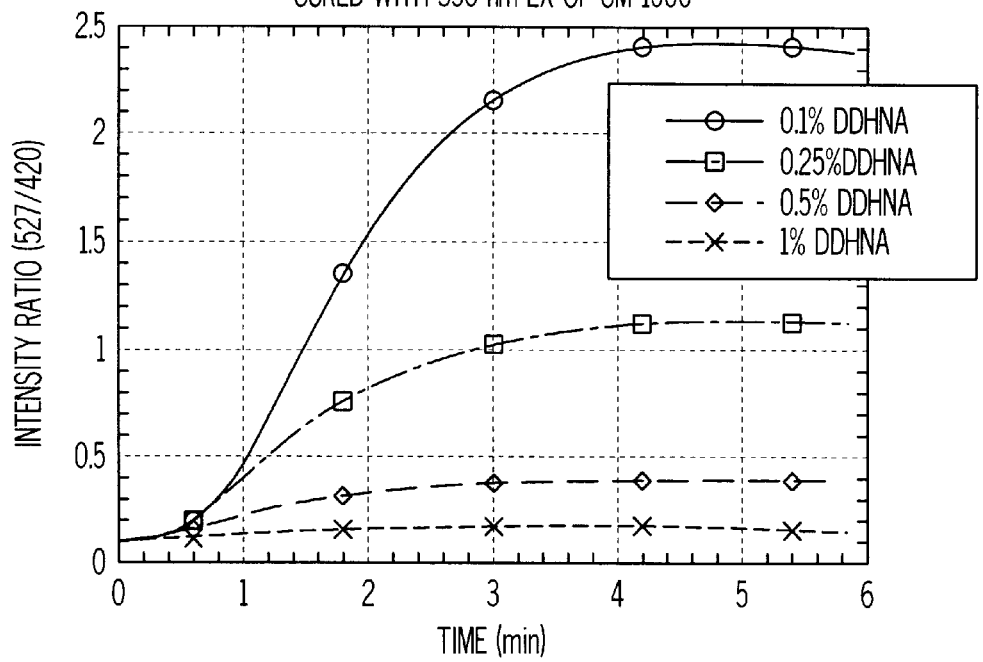
FIG. 15 shows the effect of probe concentration on ratio sensitivity. Four samples of GE Silicones epoxysilicone resin UV 9300 with 2 wt % GE Silicones photocatalyst UV9380C were cured with the 350 nm excitation of the CM 1000.

The total fluorescence intensity at the emission maximum before cure when plotted by concentration gave a linear response indicating full light penetration through the samples. As can be seen in the curing profiles shown in FIG. 15, the probe concentration greatly affected the final ratio obtained. All samples were cured as determined by hardness testing at the six minute time point. This result was very different from that observed with probes such as DASD. This indicates that a different mechanism must be involved.

Figure 16:
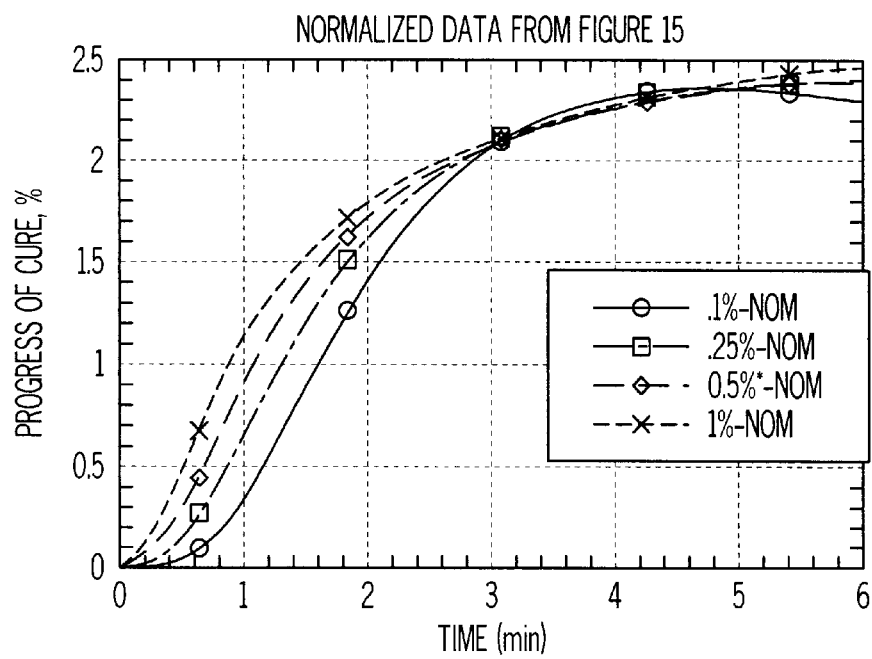
FIG. 16 shows the results of normalizing the same data as are shown in FIG. 15.

FIG. 16 shows normalized curing profiles of an epoxy-silicone resin in the presence of the same concentration of UV9300 iodonium initiator and different concentrations of the DDHNA-probe. These data indicate that with increase of the probe concentration the progress of cure at the same curing time (i.e., 1 minute) increases. Hence, the DDHNA-probe is not only useful for monitoring the polymerization progress, but also as an accelerator of the photoacid catalyst which in turn accelerates the cure speed. Accordingly, another manifestation of the invention is a curable composition (e.g., a photocurable composition) containing a compound of the formula (I) and, more particularly, a cationically curable composition containing a compound of formula (I) in combination with a compound which generates a cation upon exposure to radiation and a cationically polymerizable compound as referred elsewhere herein.

Figure 17A:
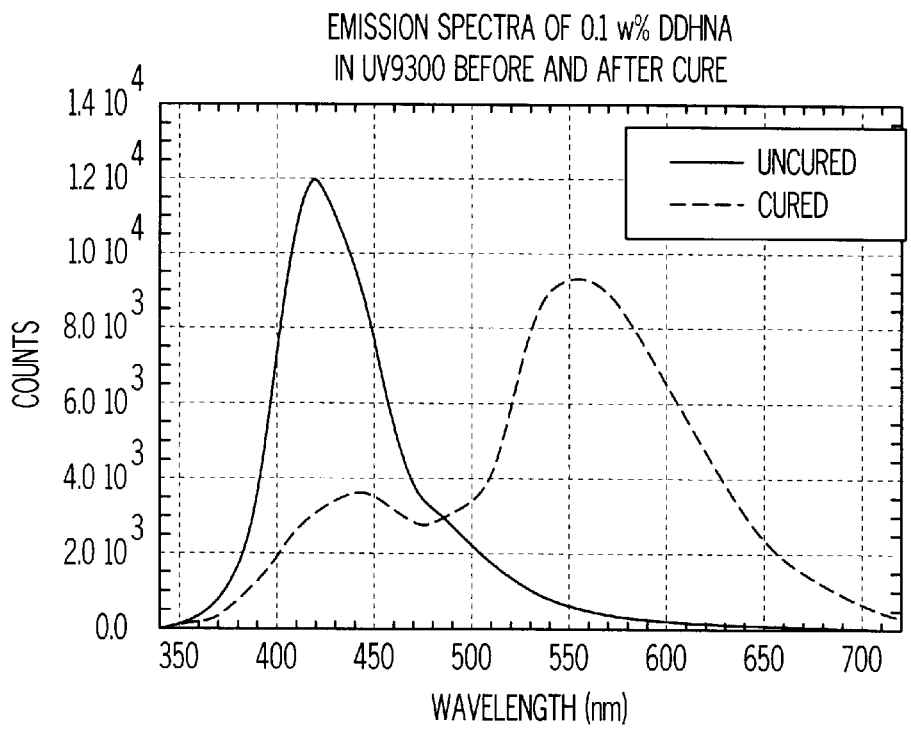
FIG. 17A shows the fluorescence emission spectra of 0.1 wt % DDHNA both before cure and after curing for 6 minutes as described in FIG. 15.
Figure 17B:
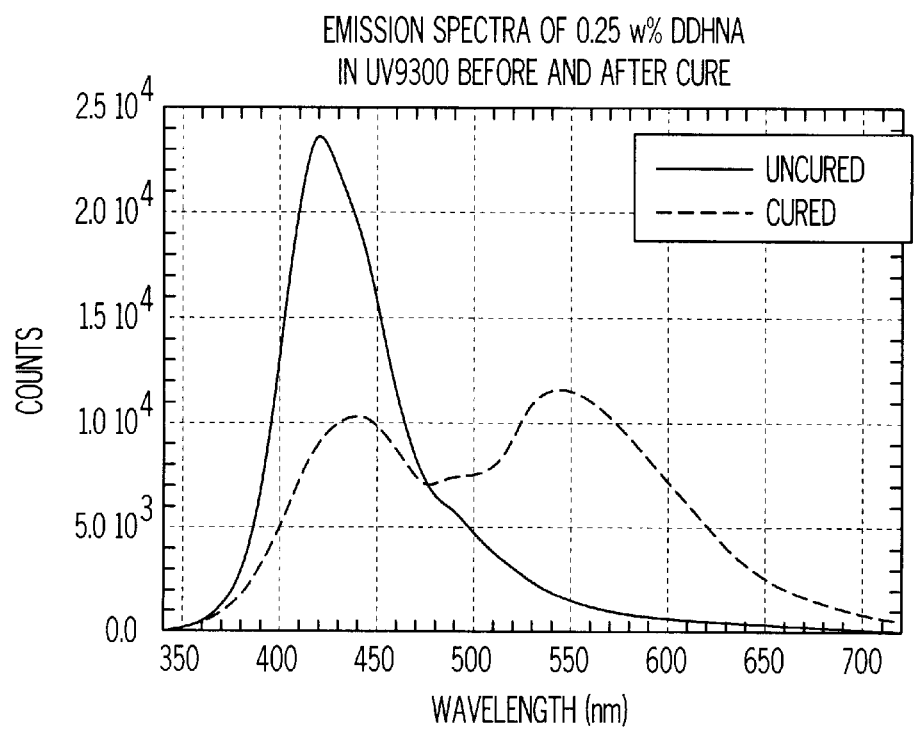
FIG. 17B shows the fluorescence emission spectra of 0.25 wt % DDHNA both before cure and curing for 6 minutes as described in FIG. 15.

The fluorescence emission spectra of the four samples both before and after cure are shown in FIGS. 17A–D. The spectra were taken for the same samples shown in FIG. 15 at 0 and 6 minutes irradiation time. As can be seen very distinctly in FIG. 17A, which is the sample containing 0.1 w % DDHNA, a new fluorescence emission band with maximum near 550 nm appears to dominate the spectrum of the cured sample, although a small peak resembling the emission band before cure, the maximum near 440 nm is still observed. This is also readily apparent in FIG. 17B for the sample containing 0.25 w % DDHNA, but in this case the intensities of the two peaks (440 nm and 540 nm) are much closer in intensity. The fluorescence emission maximum near 550 nm is less and less distinct as the concentration of probe is increased (FIGS. 17C and 17D). This marked concentration effect suggests that the probe undergoes a chemical reaction during the curing process to generate a new derivative which emits to the red of the parent DDHNA. At higher concentrations of probe this new emission band is hidden by the much larger emission from the unreacted DDHNA.

EXAMPLE 14

Figure 18:
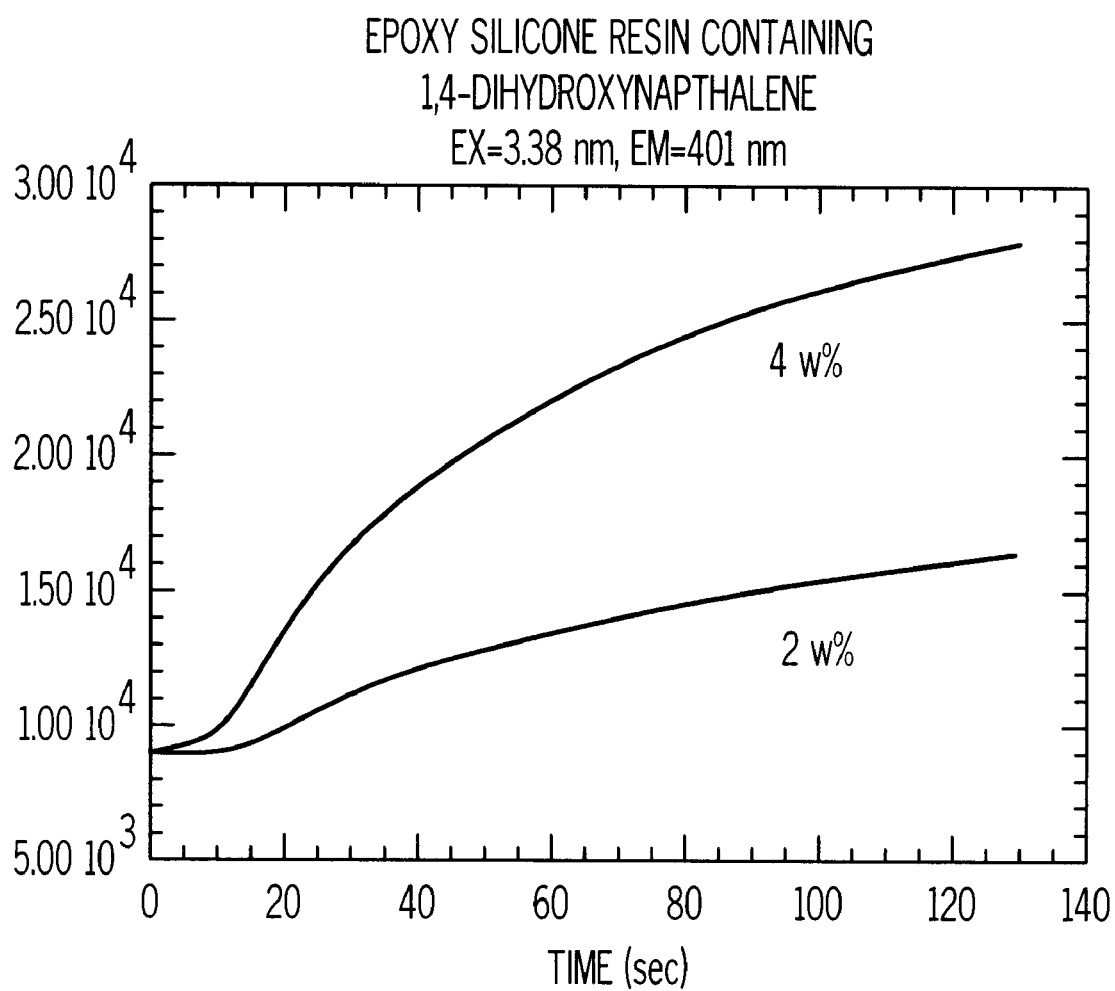
FIG. 18 illustrates the use of 1,4-dihydroxynaphthalene to monitor the cure of an epoxy silicone resin at a fluorescence emission maximum of 401 nm.

Other napthol derivatives were also evaluated for their ability to act as fluorescent probes which monitor cured ring cationic polymerization. Samples of an epoxy silicone resin containing the UV9380C initiator and either 2 or 4% of 1,4-dihydroxynapthalene were prepared as above. A drop was placed on a glass slide with 2.5 mil spacers and sample was cured with the 338 nm excitation light of the CM 1000. In this case the fluorescence emission maximum was at 401 nm and this was found to increase with cure, rather than a shift in the emission spectrum. The intensity at 401 nm is plotted versus cure time as shown in FIG. 18. The data were normalized to the first intensity to account for differences in instrument acquisition time and probe concentration. This data shows that other napthol derivatives may be useful for monitoring cure even without a spectral shift.

Having described the invention in detail with the preferred embodiment illustrated by examples and elsewhere herein, it will be apparent that modifications and variations are possible without departing from the scope of the invention defined in the appended claims.

What is claimed is:

1. A method for monitoring a property of a cationically curable composition comprising the steps of:
   adding a fluorescence probe to a cationically curable composition;
   measuring the intensity of the fluorescence emission of said probe at a wavelength at which intensity changes in response to changes occurring in said composition, wherein said fluorescence probe is a compound of the formula (I):

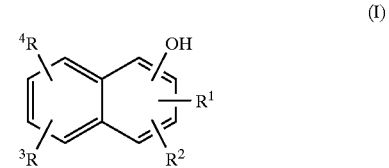

where $R^1$, $R^2$ and $R^3$ are the same or different and represent hydrogen, $C_1$–$C_{20}$ alkyl, $C_1$–$C_{20}$ alkoxyl, $C_2$–$C_{20}$ alkenyl, $C_2$–$C_{20}$ alkenoxyl, $C_3$–$C_{27}$ cycloaliphatic, $C_7$–$C_{27}$ aralkyl, $C_7$–$C_{27}$ aralkoxyl, $C_7$–$C_{27}$ alkaryl, or a substituted or unsubstituted diphenyl ether having the structure $R^9$—$C_6H_4$—O—$C_6H_4R^{10}$ where $R^9$ and $R^{10}$ may be hydrogen, alkyl, aryl or aralkyl; and $R^1$, $R^2$ and $R^3$ may be unsubstituted or may be substituted with or contain therein one or more atoms selected from the group consisting of O, S, N, OH, SH, $NH_2$, P, Cl, Br and I; and $R^4$ may be the same as $R^1$, $R^2$ and $R^3$; or $R^4$ may represent $COOR^5$, $CONR^5R^6$, $SO_2OR^5$, $SOOR^5$, $SONR^5R^6$, $S0_2NR^5R^6$ or $NR^5R^6$, where $R^5$ and $R^6$ may be hydrogen, alkyl, aryl or aralkyl;
   curing said composition;
   causing said probe to fluoresce;
   measuring the fluorescence of said probe;
   relating the change in intensity to a monitored property of said composition; and
   determining the monitored property of the composition, based upon the change in intensity.

2. The method of claim 1 wherein said step of measuring the intensity includes measuring intensity at two distinct wavelengths and calculating the ratio of the intensities and said step of relating the change in intensity includes relating the ratio to a monitored property of said composition.

3. The method of claim 1 wherein said curable composition is photocurable.

4. The method of claim 1 wherein said probe is a derivative of dihydroxynaphthalene.

5. The method of claim 4 wherein said probe is N-dodecyl-1-hydroxy-2-naphthalenecarboxamide.

6. The method of claim 3 wherein said cationically photocurable composition comprises epoxysilicones, vinyl ethers, cyclic ethers, cyclic esters, cyclic sulfides, melamine-formaldehyde, phenol-formaldehyde, lactams, lactones, cyclic acetals, epoxy compounds, vinyl ether functional prepolymers, cyclic organosiloxanes or epoxy functional silicone oligomers.

7. The method of claim 6 wherein said cationically photocurable composition comprises an epoxysilicone.

8. The method of claim 7 wherein said epoxysilicone is a dimethyl, methyl-2-(7-oxabicyclo{4.1.0}heptan-3-yl) ethyl siloxane having an epoxy equivalent weight of about 800 to 1500.

9. The method of claim 1 wherein said composition is a film or coating and said fluorescence is caused by irradiating said film or said coating with actinic radiation.

10. The method of claim 2 wherein the step of relating said ratios to the curing of said composition includes comparing said ratios to calibration data in which the curing of said composition is independently determined as a function of said ratios.

11. The method of claim 1 wherein said method is used to monitor a property selected from the group consisting of degree of cure, hardness, abrasion resistance, resistance to stain, tacticity, elasticity, molecular orientation, tensile strength, modulus, the stress state of a solid, wetness, dryness, wetability, scratch resistance, and solvent resistance.

* * * * *

UNITED STATES PATENT AND TRADEMARK OFFICE
CERTIFICATE OF CORRECTION

PATENT NO. : 5,955,002
DATED : SEPTEMBER 21, 1999
INVENTOR(S) : Neckers et al.

It is certified that error appears in the above-identified patent and that said Letters Patent is hereby corrected as shown below:

Col. 16, line 23 (claim 1) "$C_1-c_{20}$" should be --$C_1-C_{20}$--.

Signed and Sealed this

Twenty-first Day of December, 1999

Attest:

Q. TODD DICKINSON

Attesting Officer     Acting Commissioner of Patents and Trademarks